:::: {.flex}
(12) United States Patent  
Fenici

(10) Patent No.: US 6,527,724 B1  
(45) Date of Patent: Mar. 4, 2003
::::

(54) CATHETER GUIDANCE BY MAGNETOCARDIOGRAPHIC MAPPING

(75) Inventor: Riccardo Fenici, Rome (IT)

(73) Assignee: Consiglio Nazionale delle Richerche, Rome (IT)

(*) Notice: Subject to any disclaimer, the term of this patent is extended or adjusted under 35 U.S.C. 154(b) by 0 days.

(21) Appl. No.: 09/857,228

(22) PCT Filed: Dec. 6, 1999

(86) PCT No.: PCT/IT99/00402

§ 371 (c)(1),  
(2), (4) Date: Jun. 1, 2001

(87) PCT Pub. No.: WO00/33734

PCT Pub. Date: Jun. 15, 2000

(30) Foreign Application Priority Data

Dec. 4, 1998 (IT) .................................. RM98A0747

(51) Int. Cl.⁷ .............................................. A61B 8/14
(52) U.S. Cl. ................................................ 600/466
(58) Field of Search ........................ 600/466, 461, 600/459, 437, 407, 434, 435, 436, 467, 468, 469, 470

(56) References Cited

U.S. PATENT DOCUMENTS

| | | | | |
|---|---|---|---|---|
| 3,773,037 A | * | 11/1973 | Kolin ........................ 600/505 |
| 4,289,138 A | * | 9/1981 | Halvorsen ................... 600/375 |
| 4,630,611 A | * | 12/1986 | King ......................... 600/377 |
| 4,718,423 A | * | 1/1988 | Willis et al. ............... 600/325 |
| 4,785,815 A | | 11/1988 | Cohen | |
| 5,056,517 A | | 10/1991 | Fenici ....................... 128/419 P |
| 5,694,945 A | * | 12/1997 | Ben-Haim ................... 600/373 |
| 5,729,129 A | * | 3/1998 | Acker ........................ 324/207.12 |
| 5,938,602 A | * | 8/1999 | Lloyd ........................ 600/424 |
| 6,266,551 B1 | * | 7/2001 | Osadchy et al. ........... 600/424 |
| 6,298,255 B1 | * | 10/2001 | Cordero et al. ............ 600/372 |

FOREIGN PATENT DOCUMENTS

| | | |
|---|---|---|
| EP | 0 419 729 A1 | 4/1991 |
| WO | 96/41119 | 12/1996 |
| WO | 97/29678 | 8/1997 |

\* cited by examiner

*Primary Examiner*—Henry Bennett  
*Assistant Examiner*—Daniel Robinson  
(74) *Attorney, Agent, or Firm*—Ladas & Parry

(57) ABSTRACT

The catheter is constructred of a substantially cylindrical tube, longitudinally subdivided in multiple parallel lumens for wires, available to introduce drives having a distal end with a variable curving, and of fiberoptics for the delivery of energy as laser emission, or different ablation devices. The amagnetic distal electrodes permit the high-resolution mapping of multiple monophasic action potentials just at the arrthythmogenic foci themselves, the magneto cardiographic localization of the catheter and the possible modification of the electrophysiological substrate with the delivery of energy as laser emission. The catheter can be intracardiacally manipulated in the patient with a very high accuracy by exploiting the variability of the curving of the distal end and the sliding thereof into preformed external sheaths, for fitting at the best the threedimensional coordinates thereof with those of the arrhythmogenic substrate, non-invasively predetermined by magnetocardiographic imaging.

25 Claims, 5 Drawing Sheets

CATHETER GUIDANCE BY MAGNETOCARDIOGRAPHIC MAPPING

The subject matter of the present invention consists of an improved amagnetic electrocatheter for single-catheter multiple monophasic action potential recording with a high spatial resolution, directly from the arrhythmogenic substrate of a cardiac arrhythmia, and the threedimensional electro-anatomical integration of the electrophysiological information obtained on a heart model of the examined patient, andor on bi- and threedimensional magnetic resonance imaging.

The monophasic action potential recording (MAP) is a method that allows to bridge the gap between in vitro experimental electrophysiology (transmembrane action potential recording) and clinical electrophysiology. In fact, MAP allows a clinical diagnosis of the alterations in the cardiac electrogenesis, as lack of repolarization homogeneity, triggered activity, early or late afterpotentials, focal conduction abnormalities with microre-entry phenomena.

The catheter subject matter of the present invention is a multipurpose device derived from the experience with another previously patented amagnetic electrocatheter (IT 1,219;855-A EP 0,428,812 U.S. Pat. No. 5,056,517 JP 2554105), of which it constitutes an improvement.

In particular, EP 0,428,812 describes a cardiac electrocatheter which comprises a distal and proximal electrode of non-ferromagnetic, non-polarisable material adapted to being connected to external pacing devices through insulated twisted wires.

Multiple simultaneous MAP recordings are essential in order to improve the diagnostic specificity of the method.

As it is known, with the previously patented amagnetic catheter only a single MAP per catheter could be recorded. Therefore, the insertion of multiple catheters and/or the carrying out of sequential recordings, prolonging the study duration and the radioscopy times, were required. Moreover, spatial resolution was not well-defined for multiple recordings thus carried out.

The improved amagnetic electrocatheter subject matter of the present invention, by virtue of the peculiar configuration thereof and of the nature of the materials used for the construction thereof, can be used for single-catheter multiple monophasic action potential recording, although being localizable by surface magnetocardiographic mapping (MCG), with high spatial resolution and without fluoroscopy.

The electrocatheter according to the invention can have different embodiments. The most specific and innovative feature of the present device is the presence of multiple distal and proximal electrodes critically located in order to generate, sequentially or simultaneously, multiple electric or magnetic dipoles of variable intensity and geometry. This feature permits a highly accurate three-dimensional localization of the distal end (tip) of the catheter by MCG, visualizing the positioning thereof almost in real time inside a three-dimensional model of the heart of the patient under examination, interactively analyzable by the operator.

This permits to drive the catheter, by a numerical spatial control of the distal end thereof, until the three-dimensional coordinates fit at the best those of the arrhythmogenic area, with minimum use of fluoroscopy.

The magnetocardiographic driving method of the catheter onto the arrhythmogenic substrate is carried out as follows.

Prior to the invasive electrophysiological study, a magnetocardiographic study (mapping) of the patient is carried out in order to assess, even by reiterated gauging, the distribution characteristics of the magnetic field generated by the arrhythmogenic structure susceptible of catheter ablation, and the reproducible threedimensional alocalization thereof.

On the basis of such preoperating information, the amagnetic catheter is inserted under fluoroscopic control and driven in close proximity of the presumably arrhythmogenic area. Then the catheter is repositioned under magnetocardiographic spatial control, until the threedimensional coordinates of the distal end thereof fit at the best those of the target arrhythmogenic area.

Upon reaching the presumed arrhythmogenic area, the simultaneous single-catheter multiple MAP recording provides the following new electrophysiological information referring to the underlying myocardial area:

1. Estimate of the local repolarization scattering;
2. Estimate of the local conduction speed;
3. Identification of the route of the depolarization front;
4. Presence of early andor late afterpotentials;
5. Presence of areas of focal block, with or without micro re-entry; and
6. Electro-anatomical integration of the aforesaid information with the three-dimensional coordinates of the catheter distal end (tip).

Once the arrhythmogenic nature of the substrate under examination has been confirmed by high-resolution MAP mapping, energy can be outputted by laser emission with fiberoptics coaxial to and centered with respect to the area defined by the MAP recording. This allows modifying the electrogenesis of the underlying myocardium, monitoring the effects thereof according to the aforesaid parameters and to the characteristics of the arrhythmia under examination.

In case the effectiveness of a functional exclusion of the substrate under examination has been documented, this can be effectively ablated with a suitable energy output.

Hence, the electrocatheter subject matter of the present invention is aimed at the implementation of an entirely innovative approach to the electrophysiological study and to the ablation of the cardiac arrhythmiae, with high spatial resolution and minimal invasivity.

By virtue of their characteristics, the variants of the electrocatheter according to the invention are localizable by magnetocardiographic mapping, at the same time being apt to record multiple MAPs, to implement intracardiac stimulation (pacing) and to output energy by laser emission.

In its broader definition, the electrocatheter according to the invention comprises a plurality of distal electrodes, constructed of a non-ferromagnetic and non-polarizable conductor material, shaped in such a manner as to generate simultaneously or sequentially electromagnetic fields of dipolar configuration and with different geometry, at least a more proximal electrode, such electrodes being located at the end of multiple wires, of a non-ferromagnetic conductive material, which wires are electrically insulated and twisted one with respect to the other, to avoid, except for the electrodes, electromagnetic field generation along the catheter during the induction of electromagnetic dipoles at the distal end of the catheter, and a substantially cylindrical flexible tube that sheaths said wires and electrodes, at the distal end thereof leaving exposed a section of the electrode tips and, onto the side wall, near the distal end, a section of said at least one ring-shaped more proximal electrode.

Besides the lumen housing the electrodes and the wires, the flexible tube can provide a plurality of other lumens, each running along the catheter body in parallel and separate thereamong—with tip andor lateral eyelets—to insert other wires, e.g. ablation wires or biopsy tubes, or fiberoptics, or for fluid infusion and/or suction.

The equivalent surface of the electrodes ranges according to the molecular structure of the material used.

The distance between the distal electrodes and the proximal ring-shaped ones can vary.

The material used for the electrodes should be amagnetic and non-polarizable, e.g., platinated platinum or amorphous carbon. The molecular structure can be such as to increase, electrode diameters being equal, the equivalent surface.

The material used for the wires can be twisted copper, diameter about 200 $\mu$m, or other amagnetic equivalent.

The flexible tube can be made of biocompatible, non-thrombogenic plastic material. For instance, good results were obtained with materials selected from the group comprising polyurethane, polyvinyl chloride, polyether amide.

The internal gauge of the electrocatheter can range between 2.0 and 2.7 mm (6 F and 8 F, F meaning French).

All the embodiments of the amagnetic catheter according to the invention can feature a lumen available to introduce a removable system by remote control flexing of the distal end thereof.

The electrocatheter according to the present invention can be used for:

1. Single-catheter multiple monophasic action potential (MAP) intracardial mapping with high spatial resolution (Multi-MAP function);
2. Single-catheter percutaneous epicardial mapping of multiple monophasic action potentials (MAP), with high spatial resolution;
3. Magnetocardiographic localizing of catheter tip;
4. MCG-guided driving of the catheter by numerical spatial control of the distal end (tip) thereof, until the threedimensional coordinates fit at the best those of the arrhythmogenic area where the MAP recording is to be carried out;
5. Estimating the local repolarization scattering;
6. Estimating the local conduction rate;
7. Estimating the depolarization front route;
8. Obtaining an electroanatomical integration of the aforesaid information with the threedimensional coordinates of the catheter tip;
9. Outputting energy by laser emission; and
10. Supporting the guide to insert the ablation and/or biopsy wires.

A general description of the electrocatheter subject matter of the present invention has hereto been provided. Further details on the objects, features and advantages thereof will hereinafter be provided making reference to the figures referring to specific embodiments.

Figure 3A:
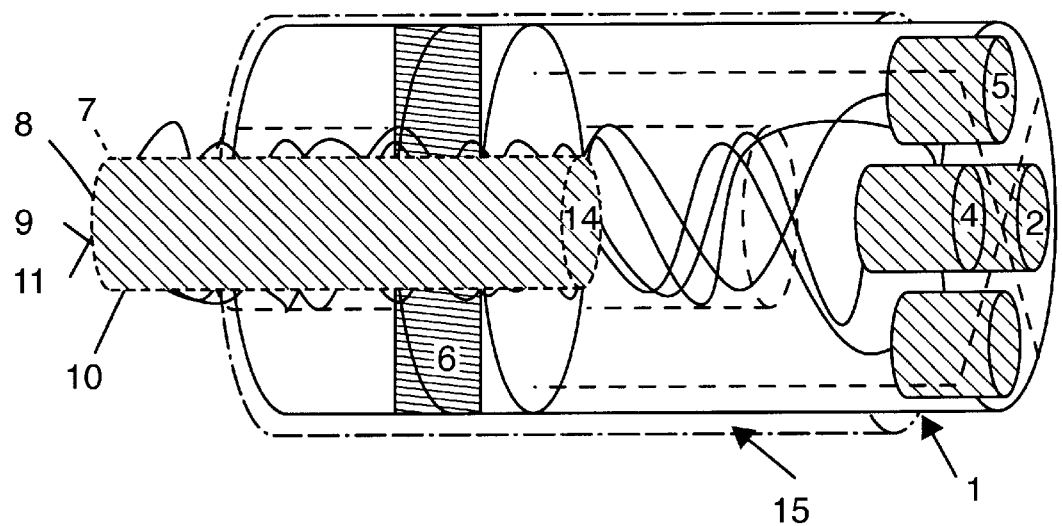
Figure 3B:
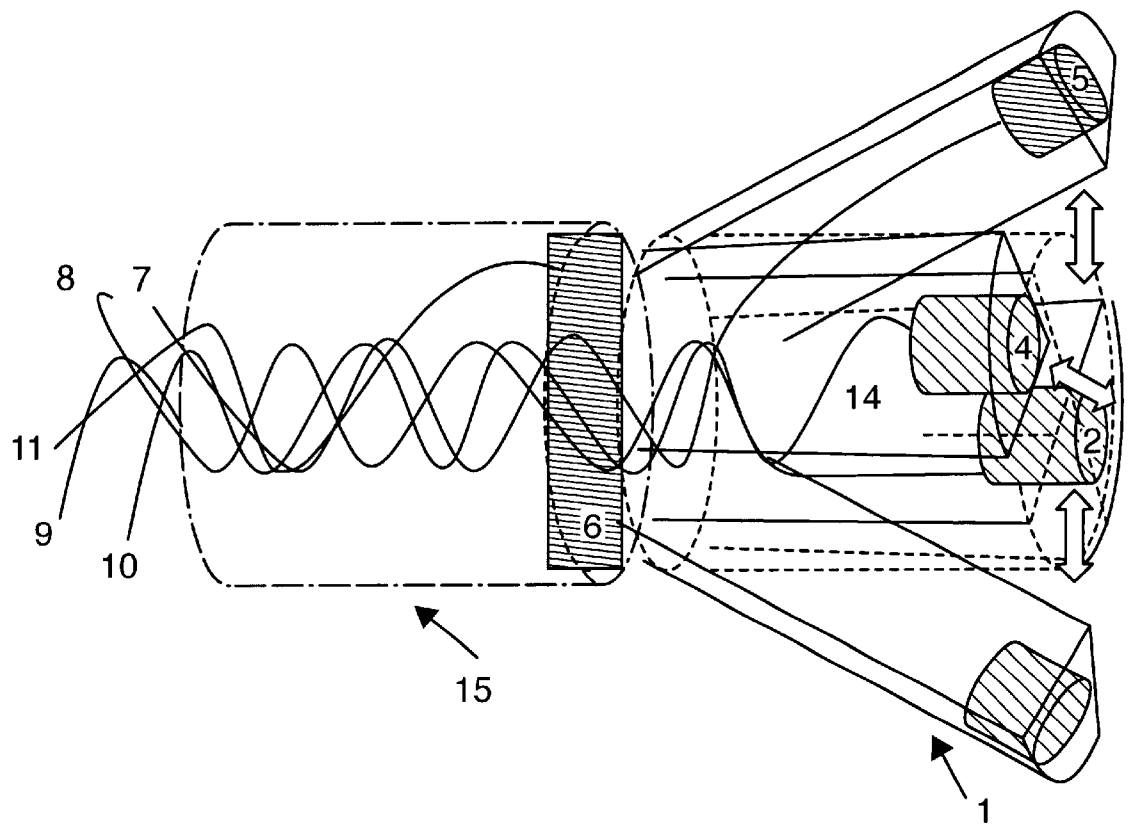
Figure 4:
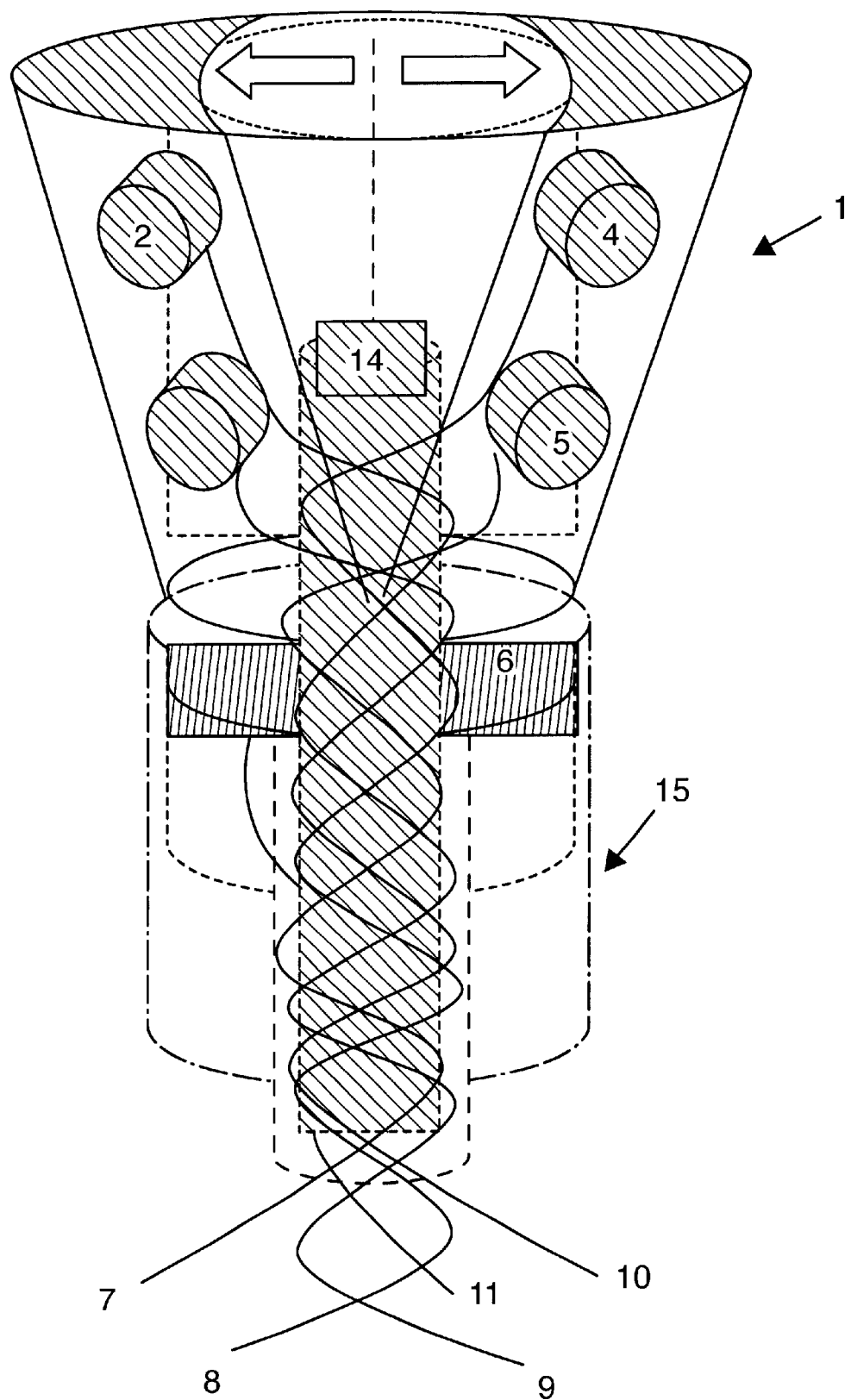
Figure 5:
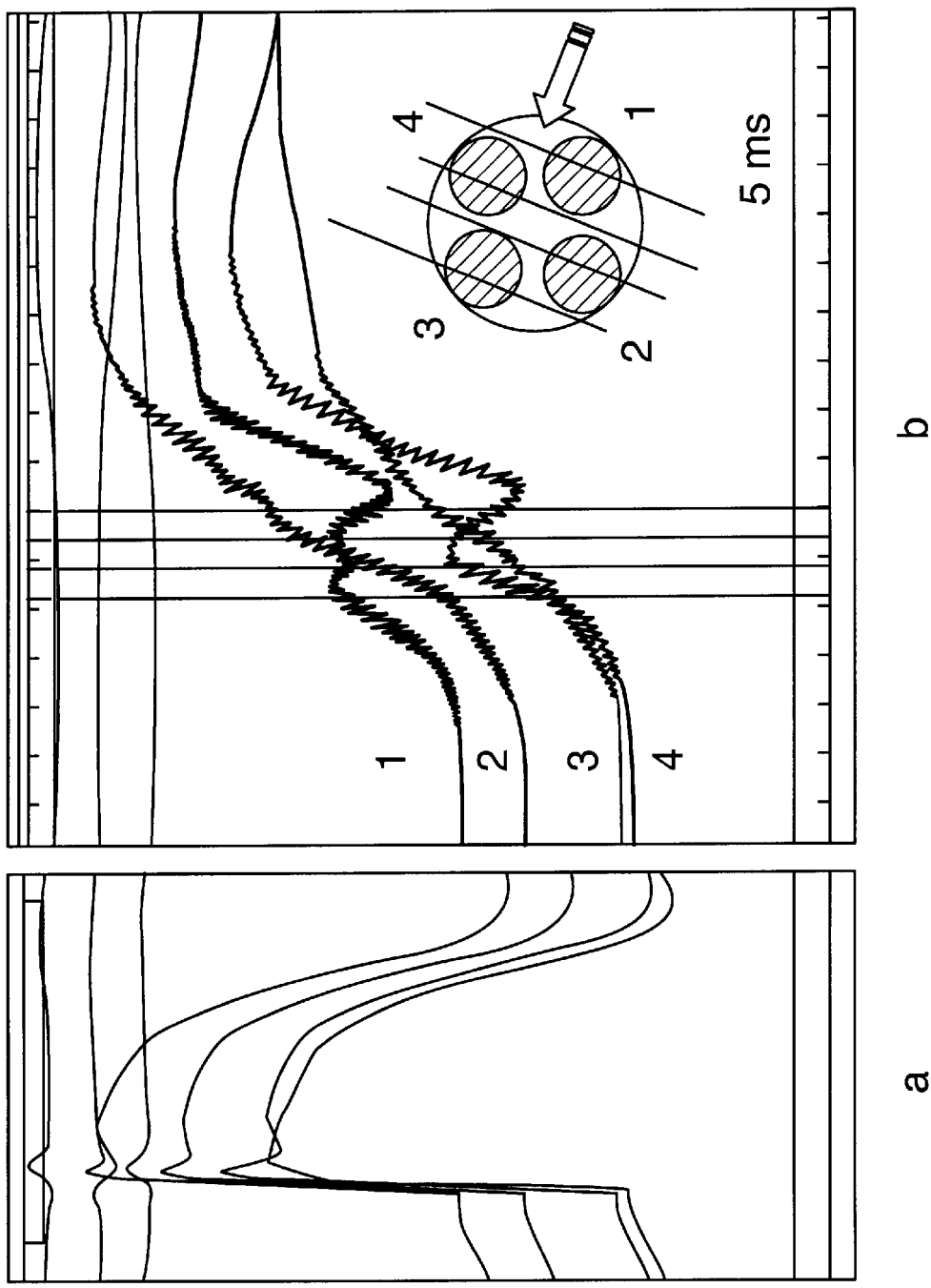

FIGS. 3a, 3b are perspective views of a third preferred embodiment of the electrocatheter according to the invention with an exemplification, depicted in different hatching, of the external sheath, of the internal coaxial lumens and of the subdivision of the distal end into four sections, in a retracted (FIG. 3a) and in a protruded (FIG. 3b) condition, according to the positioning thereof with respect to the external sheath. Moreover, the presence of coaxially and centrally located fiberoptics is exemplified;

FIG. 4 is a perspective view of a fourth preferred embodiment of the electrocatheter according to the invention, schematically similar to that in FIG. 3, but with the four distal electrodes located sideways, housed in pairs per each subdivision of the tip, and with the fiberoptics provided with a tip for energy outputting by laser emission, centered between the MAP-recording electrodes;

FIG. 5 shows an example of simultaneous recording of four MAPs (a), of the high temporal resolution analysis of the local activation time by relative temporization of the phase 0 of the four MAPs, with a schematic exemplification of the method of estimating the local propagation route of the electrical output with respect to the geometry of the catheter in cross-section (b).

Figure 1:
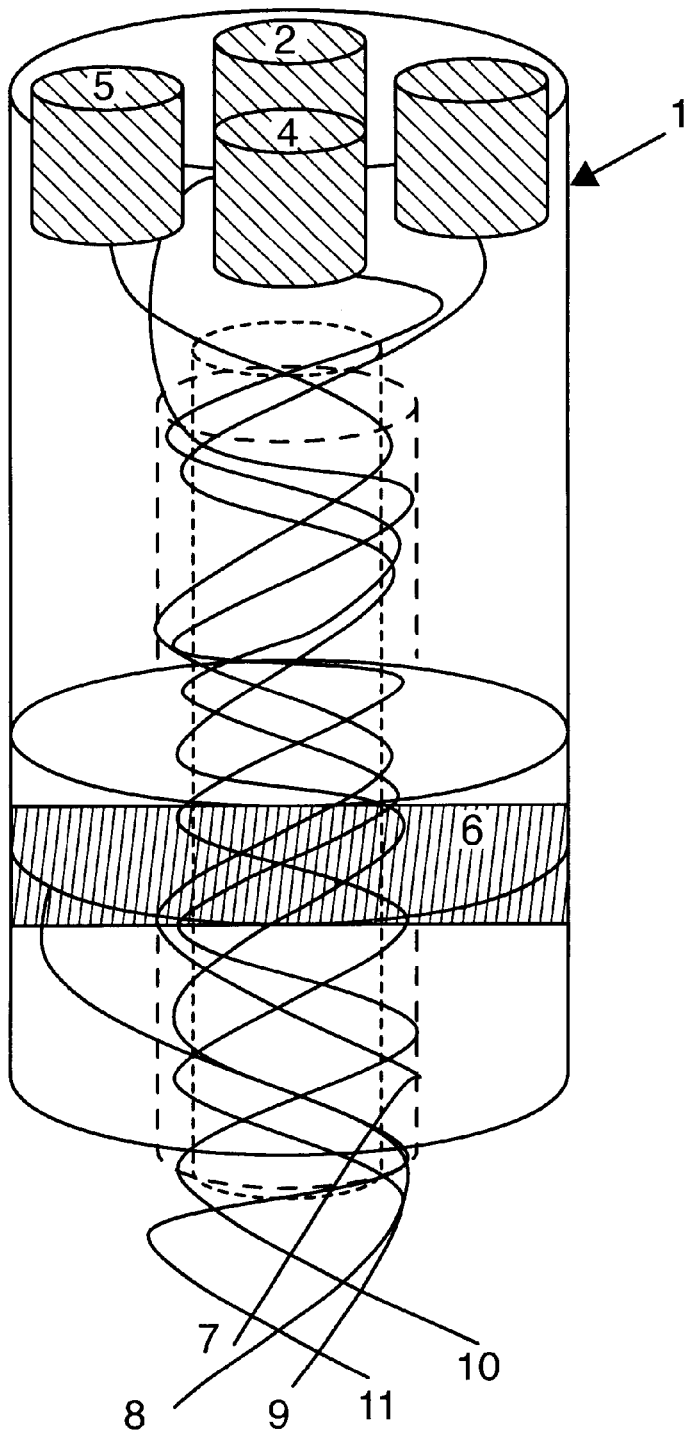
FIG. 1 is a perspective view of the tip of a preferred embodiment of the electrocatheter according to the invention, one example of the multiple internal coaxial lumens being depicted as hatched.

In the preferred embodiment of FIG. 1, the catheter has four distal electrodes of a substantially round or polygonal shape, and a more proximal substantially ring-shaped electrode. In this figure, the flexible tube in polyurethane is indicated with 1, the round-shaped distal electrodes in platinated platinum are indicated with 2, 3, 4, and 5, the ring-shaped electrode tip in platinated platinum is indicated with 6, the twisted copper wires (diameter about 200 $\mu$m), connected to the four distal electrodes 2 to 5 and to the ring-shaped proximal electrode 6 respectively, are indicated with 7, 8, 9, 10 and 11. The diameter of the electrodes 2 to 5 ranges between 400 and 600 $\mu$m. The equivalent surface of the electrodes 2 to 5 can vary depending on the molecular structure of the material used. The distance between the distal electrode tips is comprised between 1.5 and 2 mm, and that between the distal electrode tips and the ringshaped proximal electrode can range between 2 and 7 mm. The internal catheter size ranges between 2.0 and 2.7 mm (6 to 8 F).

Figure 2:
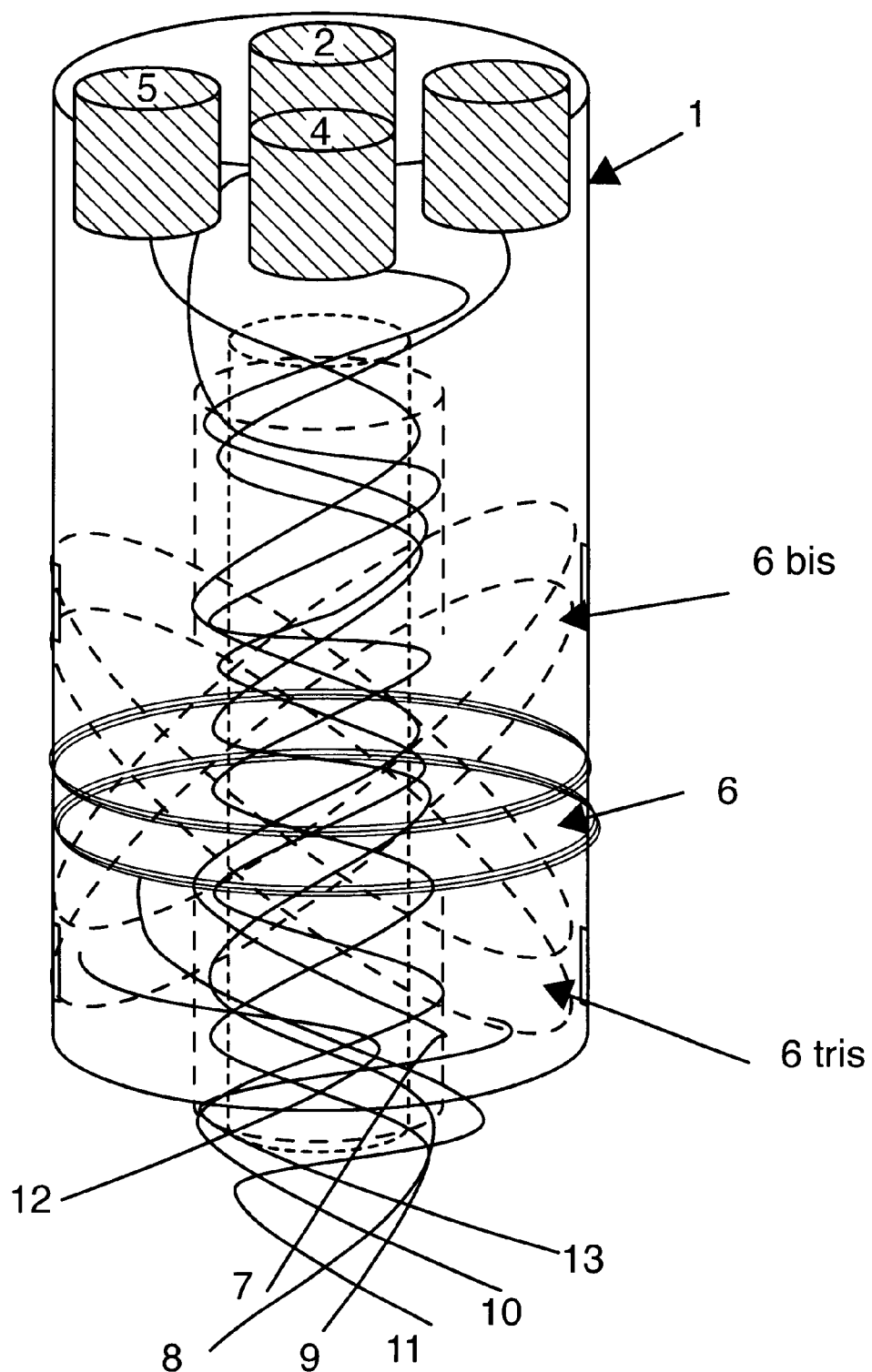
FIG. 2 is a perspective view of a second preferred embodiment of the electrocatheter according to the invention, with three distal ring-shaped electrodes differently oriented thereamong, each connected to two wires, located at the distal end thereof.

In FIG. 2, a second preferred embodiment of the catheter is shown, in all similar to the one in FIG. 1, but having three ring-shaped proximal electrodes differently oriented thereamong, indicated with 6, 6 bis and 6 tris, the respective wires thereof being 11, 12 and 13.

In FIG. 3 a third preferred embodiment of the catheter is shown, here it being sheathed and sliding into a thin external sheath, having the tip subdivided lengthwise for some millimeters into four parallel sections, flexible and preformed, so that when the catheter is completely retracted inside the external sheath the four distal electrode tips, each housed inside one of the four subsections, are near as in the preceding embodiment (FIG. 3a); whereas when the catheter is pushed out from the external sheath the four subsections of the tip thereof diverge thereamong, thereby increasing the distance between the distal electrodes (FIG. 3b). In FIG. 3, the flexible tube in polyurethane is indicated with 1, the distal section thereof being longitudinally subdivided into four equal sectors, each bearing one of the round- or polygon-shaped distal electrodes 2, 3, 4, and 5 in platinated platinum, the ring-shaped electrode tip in platinated platinum is indicated with 6, the twisted copper wires of about 200 $\mu$m connected to the four distal electrodes 2 to 5 and to the ring-shaped proximal electrode 6, are indicated with 7, 8, 9, 10 and 11, respectively. The diameter of the electrodes 2 to 5 ranges from 400 to 600 $\mu$m. The equivalent surface of the electrodes 2 to 5 can range according to the molecular structure of the material used. An external thin sheath in a plastic biocompatible material inside which the catheter can slide to measure is indicated with 15. When the catheter is retracted inside the sheath (FIG. 3a), the tip thereof is closed and the gauge of the catheter can range between 2 and 2.7 mm (6–8 F). In this condition the distance between the electrode tips ranges between 1.5 and 2 mm. When the catheter is pushed out of the sheath (FIG. 3b) the four sections of the tip thereof diverge and the distance between the electrode tips ranges between 4 and 5 mm. The distance between the distal electrodes and the proximal electrode can range between 2 and 7 mm. Two coaxial lumens for infusion, suction or introduction of a guide having a flexible apex can be seen hatched at the center of the catheter. In the example, the innermost lumen houses fiberoptics (14) for laser ablation.

In FIG. 4 a fourth preferred embodiment of the catheter is depicted, having the four end electrodes protruding sideways from one side only, housed in pairs for each subdivision of the distal end longitudinally subdivided for several mm into two parallel, flexible and preformed sections, so that when the catheter is completely retracted inside the external sheath the four electrode tips are nearer, whereas when the catheter is pushed out of the external sheath the two end subsections diverge, thus increasing the distance between the electrode tips. In FIG. 4, the flexible tube in polyurethane is indicated with 1, the distal end section thereof being longitudinally subdivided into two equal sectors, each bearing two of the electrode tips, located onto the side wall and spaced between about 3 and 5 mm, at open tip. The shape, the section and the material of the electrodes and of the wires, as well as the nomenclature thereof remains unaltered with respect to the embodiment shown in FIG. 3.

To the above described improved amagnetic catheter a person skilled in the art, in order to satisfy further and contingent needs, may effect several further modifications and variants, all however comprised within the scope of the present invention, as defined by the annexed claims.

What is claimed is:

1. A cardiac electrocatheter comprising a plurality of distal electrodes (2, 3, 4, 5), constructed of a non-ferromagnetic and non-polarizable conductor material, shaped in such a manner as to generate simultaneously or sequentially electromagnetic fields of dipolar configuration and with different geometry, at least a more proximal electrode (6; 6bis; 6tris), such electrodes being located at the end of multiple wires (7, 8, 9, 10, 11, 12, 13), of a non-ferromagnetic conductive material, which wires are electrically insulated and twisted one with respect to the other, to avoid, except for the electrodes, magnetic field generation along the catheter during the induction of electromagnetic dipoles at the distal end of the catheter, and a substantially cylindrical flexible tube (1) that sheaths said wires and electrodes, at the distal end thereof leaving exposed a section of the electrode tips and, onto the side wall, near the distal end, a section of said at least one ring-shaped more proximal electrode.

2. The cardiac electrocatheter as per claim 1, wherein at least a further lumen is available for the insertion of fiberoptics (14) or guides of variable geometry.

3. The cardiac electrocatheter as per claim 1, wherein the catheter has four substantially round-shaped or polygon-shaped distal electrodes, and multiple substantially ring-shaped proximal electrodes differently oriented with respect to the longitudinal axis of the catheter.

4. The cardiac electrocatheter as per claim 3, wherein said ring-shaped electrodes have a single or twin wire.

5. The cardiac electrocatheter as per in claim 1, wherein the distal end thereof is longitudinally divided for some millimeters into four flexible and preformed sections and is provided with an external sheath inside which it can slide in such a way that when the catheter is completely retracted inside the external sheath the four distal electrodes, each housed inside one of the four subsections, are substantially parallel, whereas when the catheter is pushed out of the external sheath the four terminal subsections diverge, increasing the distance between the electrode tips.

6. The cardiac electrocatheter as per in claim 5, wherein the distal end thereof is longitudinally divided for more than two millimeters into said four sections.

7. The cardiac electrocatheter as per claim 1, wherein the tip thereof is longitudinally divided for several millimeters into two parallel, flexible and preformed sections and with the four terminal electrodes protruding sideways from one side, housed in pairs inside each subdivision of the tip.

8. The cardiac electrocatheter as per claim 7, wherein the tip thereof is longitudinally divided for more than two millimeters into said two sections.

9. The cardiac electrocatheter as per claim 1, wherein the equivalent surface of the electrodes can vary according to the molecular structure of the material used.

10. The cardiac electrocatheter as per claim 1, wherein the distance between the distal and the more proximal ring-shaped electrodes can vary.

11. The cardiac electrocatheter as per claim 1, wherein the material of which the electrodes are constructed is amagnetic and non-polarizable, and is selected from the group comprising platinated platinum and amorphous carbon, the molecular configuration thereof being variable in such a way as to increase, electrode diameters being equal, the equivalent surface.

12. The cardiac electrocatheter as per claim 1, wherein the material of the wires is an amagnetic material.

13. The cardiac electrocatheter as per claim 1, wherein the flexible tube is constructed of a non-thrombogenic plastic biocompatible material.

14. The cardiac electrocatheter as per claim 13, wherein said material is selected from a group comprising polyurethane, polyvinyl chloride and polyetheramide.

15. The cardiac electrocatheter as per claim 1, wherein the internal gauge of the electrocatheter ranges between 1.7 and 2.7 mm (from 6F to 8F).

16. The cardiac electrocatheter as per claim 1, wherein, besides the lumen housing the electrodes and the wires, the flexible tube is provided with a plurality of other lumens, each running along the body of the catheter in parallel and separate from the others—with terminal or lateral eyelets—for inserting other wires, e.g. for ablation or biopsy, or fiberoptics, or for infusion and/or suction.

17. The use of the electrocatheter as per claim 1, for the single-catheter intracardiac mapping of multiple monophasic action potentials (MAPs), with high spatial resolution (Multi-MAP function).

18. The use of the electrocatheter as per claim 1, by single-catheter percutaneous epicardial mapping of multiple monophasic action potentials (MAPs), with high spatial resolution.

19. The use of the electrocatheter as per claim 1, for the magnetocardiographic localization of the catheter tip.

20. The use of the electrocatheter as per claim 1, for MCG-guided drive of the catheter by numerical spatial control of the distal end thereof, until the three-dimensional coordinates fit at the best those of the arrhythmogenic area where the MAPs recording is to be carried out.

21. The use of the electrocatheter as per claim 1, for the automatic estimate of the local scattering of the repolarization.

22. The use of the electrocatheter as per claim 1, for the automatic estimate of the local conduction speed.

23. The use of the electrocatheter as per claim 1, for the automatic estimate of the route of the local depolarization front.

24. The use of the electrocatheter as per claim 1, for the electroanatomical integration of the aforesaid information with the three-dimensional coordinates of the catheter tip.

25. The use of the electrocatheter as per claim 1, for the output of energy by laser emission.

* * * * *